(12) United States Patent
Nasry

(10) Patent No.: US 11,786,161 B2
(45) Date of Patent: Oct. 17, 2023

(54) GARMENT MEDICAL EXAMINATION SYSTEM

(71) Applicant: Samer Nasry, Franklin, MI (US)

(72) Inventor: Samer Nasry, Franklin, MI (US)

( * ) Notice: Subject to any disclaimer, the term of this patent is extended or adjusted under 35 U.S.C. 154(b) by 428 days.

(21) Appl. No.: 17/064,121

(22) Filed: Oct. 6, 2020

(65) Prior Publication Data

US 2022/0104721 A1    Apr. 7, 2022

(51) Int. Cl.
| | | |
|---|---|---|
| *A61B 5/00* | (2006.01) | |
| *A61B 5/28* | (2021.01) | |
| *A61B 5/282* | (2021.01) | |
| *A61B 5/0205* | (2006.01) | |
| *A61B 5/1455* | (2006.01) | |
| *A61B 7/04* | (2006.01) | |
| *A61B 5/316* | (2021.01) | |
| *A61B 5/339* | (2021.01) | |
| *A61B 5/022* | (2006.01) | |

(52) U.S. Cl.
CPC ............ *A61B 5/282* (2021.01); *A61B 5/0006* (2013.01); *A61B 5/0057* (2013.01); *A61B 5/0205* (2013.01); *A61B 5/14552* (2013.01); *A61B 5/316* (2021.01); *A61B 5/339* (2021.01); *A61B 5/6804* (2013.01); *A61B 5/6806* (2013.01); *A61B 5/6826* (2013.01); *A61B 5/6891* (2013.01); *A61B 7/04* (2013.01); *A61B 5/02233* (2013.01); *A61B 2562/0247* (2013.01)

(58) Field of Classification Search
CPC .............. A61B 5/1455; A61B 5/14551; A61B 5/14552; A61B 5/68; A61B 5/681; A61B 5/6804; A61B 5/6806; A61B 5/6826; A61B 5/6891; A61B 5/02233
See application file for complete search history.

(56) References Cited

U.S. PATENT DOCUMENTS

| | | | |
|---|---|---|---|
| 6,425,862 B1 * | 7/2002 | Brown | A47C 31/126 600/300 |
| 7,156,808 B2 | 1/2007 | Quy | |
| 7,249,036 B2 | 7/2007 | Bayne | |
| 9,208,288 B2 | 12/2015 | Putrino | |
| 9,872,628 B2 * | 1/2018 | Hyde | A61B 5/02438 |
| 2002/0045805 A1 * | 4/2002 | Gopinathan | A61B 5/6806 128/903 |
| 2002/0111777 A1 | 8/2002 | David | |
| 2009/0171166 A1 | 7/2009 | Amundson et al. | |
| 2013/0172691 A1 | 7/2013 | Tran | |

(Continued)

FOREIGN PATENT DOCUMENTS

| | | |
|---|---|---|
| EP | 2744403 A1 | 6/2014 |
| EP | 3202320 A1 | 8/2017 |

OTHER PUBLICATIONS

PCT Search Report & Written Opinion dated Apr. 25, 2019, Application No. PCT/US2019/016314.

*Primary Examiner* — Chu Chuan Liu

(74) *Attorney, Agent, or Firm* — Young Basile Hanlon & MacFarlane, P.C.

(57) ABSTRACT

A glove comprising a set of electrocardiogram leads, the set of electrocardiogram leads including: (a) a plurality of precordial electrocardiogram leads; (b) a pair of aVL and aVR electrocardiogram leads; and (c) an aVF electrocardiogram lead; wherein the glove records a 12-lead electrocardiogram by pressing the glove against skin of a user.

20 Claims, 5 Drawing Sheets

(56) References Cited

U.S. PATENT DOCUMENTS

| | | | |
|---|---|---|---|
| 2013/0267818 A1* | 10/2013 | David | A61B 5/0006 |
| | | | 600/382 |
| 2014/0143064 A1 | 5/2014 | Tran | |
| 2016/0256104 A1 | 9/2016 | Romem et al. | |
| 2016/0360965 A1 | 12/2016 | Koninklijke | |
| 2017/0000369 A1* | 1/2017 | Hyde | A61B 5/6806 |
| 2018/0132815 A1 | 5/2018 | Tsai | |
| 2019/0231262 A1* | 8/2019 | Nasry | A61B 7/026 |

* cited by examiner

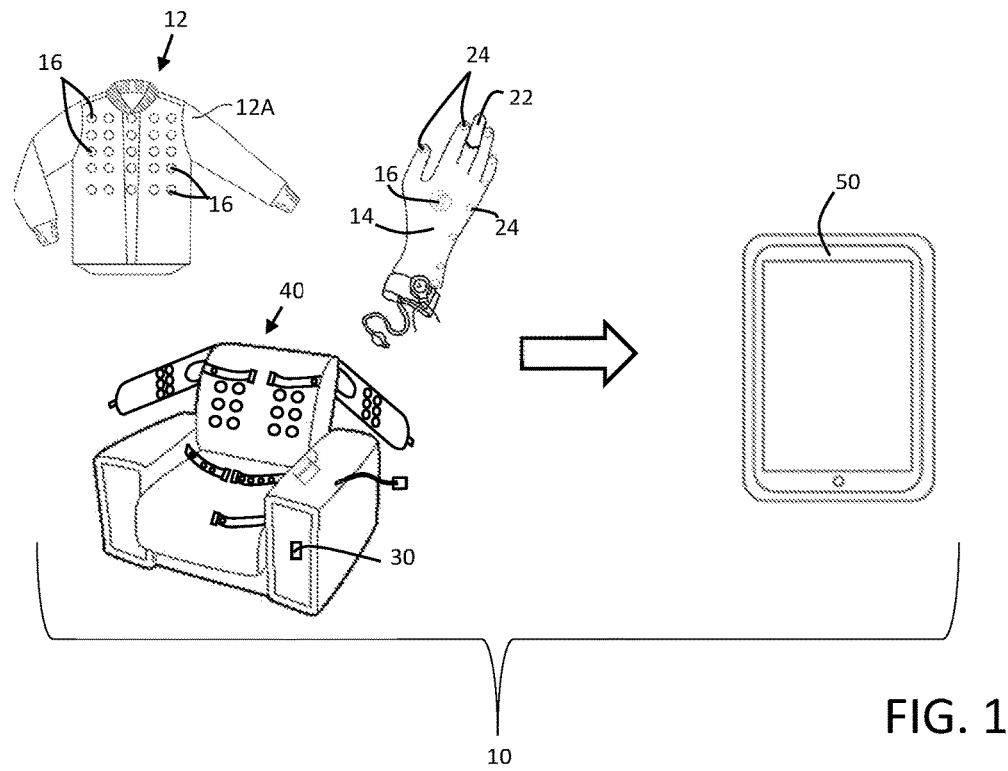
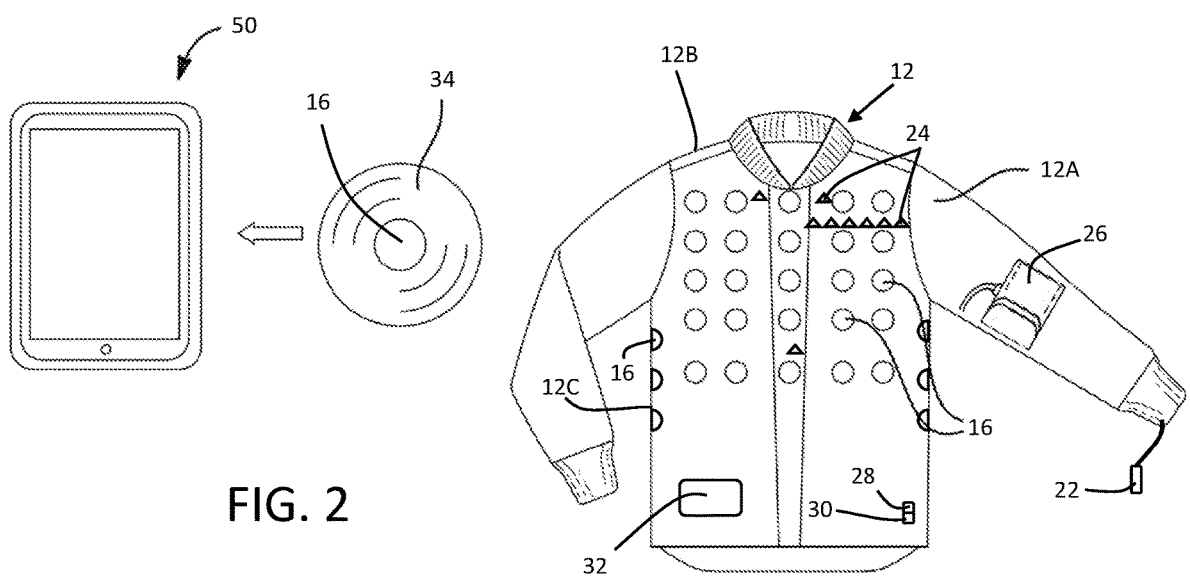
FIG. 1
FIG. 2

GARMENT MEDICAL EXAMINATION SYSTEM

FIELD

The present teachings generally relate to devices and systems for performing physical medical examinations, and more particularly, to wearable garments and an associated system that measures and monitors vital signs to treat various health conditions.

BACKGROUND

An increased cost of healthcare coupled with increases in population and patient age have led to significant developments in remote medical treatment devices. These remote medical devices help facilitate medical treatment of patients who can or do not physically travel to a medical office or hospital. As a result, more patients, such as those incapacitated or house-ridden, are able to receive more thorough medical care, resulting in various health conditions being detected and treated at an earlier stage—prior to the health condition reaching a point where hospitalization is necessary.

These remote medical treatment devices may often involve a transmission of medical records (i.e., past medical history, allergies, medications) along with patient medical data from a patient location to a central medical facility. The central medical facility may then evaluate the records and data to determine if any health condition is present in the patient that requires treatment. After evaluation, the central medical facility may communicate with the patient any treatment plan or further steps needed.

However, remote medical treatment devices are often inaccurate or over-simplified for patient use. As a result, the medical data transmitted to the central medical facility may be significantly limited or incorrect, resulting in frequent misdiagnosing of health conditions or inadvertently overlooking a health concern of a patient. Furthermore, because the remote medical treatment devices may be rather limited in functionality, medical professionals may be hesitant to offer remote communication or still require a patient to physically visit a medical office, even after remote data collection.

There remains a need for a medical device system that accurately records and transmits medical data from a patient to an external location. What is needed is a medical device system that includes one or more wearable garments having a plurality of sensors that accurately receive data from a patient and transmit that data to an external location. Additionally, there remains a need for a medical device system easy and simple enough for a patient to operate independently of a medical professional. What is needed is a medical device system that includes one or more wearable garments that track patient data in a streamlined fashion. Moreover, there remains a need for a medical device system that robustly collects a plurality of vitals from a patient to accurately evaluate the data for any potential health concerns. Thus, what is needed is a medical device system having a plurality of interconnected sensors and devices that detect and record extensive vitals of a patient. Additionally, there remains a need for a medical device system that remotely and accurately records heart and lung auscultation of a patient.

SUMMARY

The present teachings meet one or more of the present needs by providing a glove comprising a set of electrocardiogram leads, the set of electrocardiogram leads including: (a) a plurality of precordial electrocardiogram leads (e.g., V1-V6); (b) a pair of aVL and aVR electrocardiogram leads; and (c) an aVF electrocardiogram lead; wherein the glove records a 12-lead electrocardiogram by pressing the glove against skin of a user.

The present teachings may also meet one or more of the present needs by providing a glove, wherein: the plurality of precordial electrocardiogram leads are positioned along a peripheral edge of the glove; the pair of aVL and aVR electrocardiogram leads are positioned on fingertips of a thumb and an index finger of the glove; the aVF electrocardiogram lead is positioned on a fingertip of a ring finger of the glove; the glove records the 12-lead electrocardiogram by recording data from the set of electrocardiogram leads in 3 or 4 distinct positions of the glove in contact with the skin of the user; the plurality of precordial electrocardiogram leads record data in a first position of the glove, whereby the glove is disposed substantially horizontally along the chest of the user with the plurality of precordial electrocardiogram leads in contact with the chest of the user; the pair of aVL and aVR electrocardiogram leads record data in a second position of the glove, whereby the glove is disposed substantially vertically along the chest of the user with the fingertips of the thumb and the index finger spaced apart and in contact with the chest of the user; the thumb and the index finger of the glove form an angle of at least 100 degrees when in the second position; the aVF electrocardiogram lead records data in a third position of the glove, whereby the glove is disposed substantially vertically along the abdomen of the user with the fingertip of the ring finger in contact with the abdomen of the user; or a combination thereof.

Furthermore, the present teachings meet one or more of the present needs by providing a glove that includes a blood pressure cuff, a pulse oximeter integrally formed, or connected to, a middle finger of the glove, a digital microphone positioned centrally along the glove, or a combination thereof. Additionally, the 12-lead electrocardiogram recorded by the glove may be wirelessly transmitted from the glove to an external computing device, wherein data recorded by the glove is processed through a filtration step, an amplification step, or both before being displayed on the external computing device for evaluation. The data recorded by the glove and transmitted to the external computing device may be displayed in a report. Moreover, the glove may be worn by the user to record their own 12-lead electrocardiogram.

The present teachings may also meet one or more of the present needs by providing a medical device system, including: (a) a glove; (b) a wearable garment having a plurality of microphones; (c) a club including one or more tapping mechanisms that create a percussion through a patient's body; and (d) a chair having one or more sensors; wherein data is recorded by the glove, the garment, the chair, or a combination thereof and wirelessly transmitted to a computing device for offsite evaluation. The plurality of microphones of the garment may record sounds to compile a sound pulmogram, a sound cardiogram, or both. The plurality of microphones may be site specific such that each sound record is associated with a specific microphone location. Moreover, the chair may include one or more pressure sensors, one or more air compartments, one or more microphones, or a combination thereof.

Moreover, the present teachings meet one or more of the present needs by providing: a medical device system that accurately records and transmits medical data from a patient to an external location; a medical device system that includes one or more wearable garments having a plurality of sensors that accurately receive data from a patient and transmit that data to an external location; a medical device system easy and simple enough for a patient to operate independently of a medical professional; a medical device system that includes one or more wearable garments that track patient data in a streamlined fashion; for a medical device system that tracks robustly collects a plurality of vitals from a patient to accurately evaluate the data for any potential health concerns; a medical device system having a plurality of interconnected sensors and devices that detect and record extensive vitals of a patient; a medical device system that remotely and accurately records heart and lung auscultation of a patient; or a combination thereof.

BRIEF DESCRIPTION OF THE DRAWINGS

FIG. 1 is a perspective view of a medical device system.

FIG. 2 is a perspective of a garment having a plurality of microphones.

DETAILED DESCRIPTION

Figure 3:
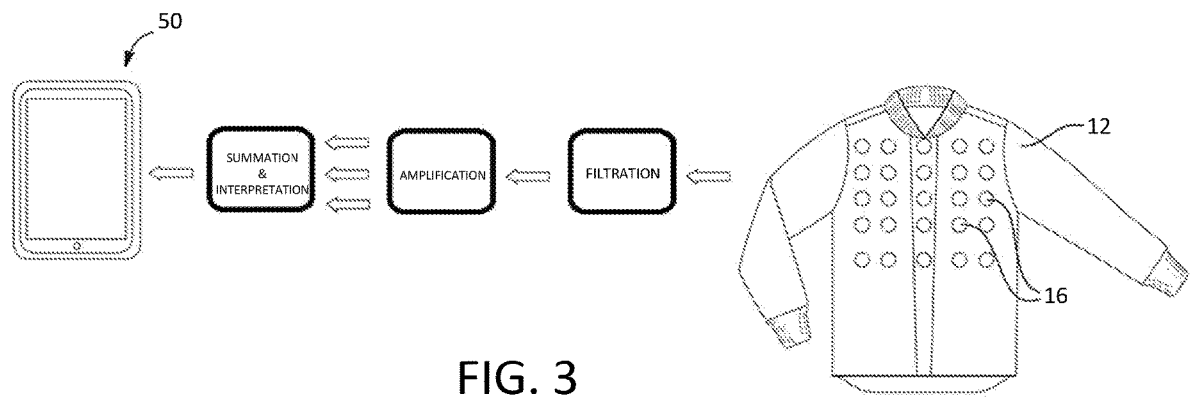
FIG. 3 is a process flowchart illustrating the processing of recorded data from a garment.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings generally relate to a medical device system. The medical device system may function to identify, measure, or both an extensive range of vital and physical examination signs of a patient for remote medical care. It is envisioned that the medical device system described herein provides medical professionals and patients alike the ability to record data based upon a specific patient in order to properly evaluate a variety of health conditions without requiring a patient to be physically present in a medical facility. For example, the medical device system may be utilized for patients that are incapacitated or otherwise unable to travel to a medical facility, such as a hospital or a physician's office, to evaluate potential health risks while the patient remains a home—all without jeopardizing the level of healthcare expected when a patient enters an actual medical facility. Additionally, it is envisioned that the medical device system may facilitate healthcare of patients remotely without exposing those patients to potential health risks in a medical facility, such as those present during a pandemic.

The medical device system may include a number of devices interconnected to form the system. The medical device system may include one or more wearable components, one or more accessories, one or more electronic devices, or a combination thereof. Advantageously, all or only a portion of the devices within the medical device system may be utilized for a specific application. For example, all devices may be utilized to compile data based on a patient more at risk of health complications while minor evaluations may only utilize a single device within the medical device system. Thus, it may be gleaned from the present teachings that the medical device system is highly customizable and portable for a number of different remote applications.

The medical device system may include a garment. The garment may function to provide at least a partial medical evaluation of a patient by recording, tracking, or otherwise collecting key medical data. The garment may then transfer such data offsite from a patient's location (e.g., the patient's home) to an offsite physician, to a computer-based medical system, or the like. The garment described herein may be utilized by any patient desiring examination and treatment for most medical conditions while remaining in the comfort of their own home. The patient self-testing using the garment may conduct as thorough, or even more thorough, an analysis than an in-office doctor visit. The results of the self-exam may be easily transmitted to the home medical software or a medical professional where it can be determined if further tests are required, a prescription is required, a specialist is required, if immediate medical attention is necessary, or a combination thereof. The garment may be similar to those described in U.S. patent application Ser. No. 16/265,339, all of which is incorporated herein for all purposes.

The garment may be shaped as a jacket, a vest, a wrap, a poncho, or the like. The garment may include a plurality of electrocardiogram leads, a plurality of auscultation acoustic sensor devices located in one or more of an anterior chest wall, posterior chest wall, anterior abdominal section, posterior abdominal section, or any combination thereof to provide optimal heart and lungs auscultation, a flexible respiratory sensor, one or more cuff portions (e.g., blood pressure cuff portions) located on an at least one arm portion of the garment, and a hardware device for sending and receiving signals via wired or wireless communication. The garment may include a section that contacts a patient's abdomen. The garment may include a section that contacts a patient's lower back. The garment may include a plurality of devices that are removably connected to or work in tandem with the garment. These devices may include but are not limited to: a pulse oximeter, otoscope, oralscope, ophthalmoscope, PanScope, and oral temperature device.

The garment may include a plurality of auscultation acoustic sensor devices or other microphones anywhere along the garment. The microphones may collect data from a patient by recording sound coming from one or more internal organs of the patient. The microphones may be strategically arranged in a manner which forms a blanket that hugs the patient thorax providing optimal heart and lungs auscultation. The auscultation acoustic sensor devices (e.g. microphones; stethoscopes) may be utilized to record one or more of a patient's lung sounds including but not limited to clear breathing sounds, reduced breathing sounds, diffuse wheezing, basilar crackles, and scattered rhonchi, or absence of breathing sounds. The auscultation acoustic sensor devices (e.g. microphones, stethoscopes, or the like) may be utilized to record one or more of a patient's heart and lung sounds including but not limited to: normal heart sounds; S1 heart sound; S2 heart sound; murmurs; aortic stenosis; mitral regurgitation; pulmonic stenosis; aortic insufficiency, any other heart valve and/or heart muscle disease, any other lung disease, or a combination thereof. The auscultation acoustic sensor devices may provide a description of the location, strength, type, and quality of the recorded sound. The auscultation acoustic sensor devices may be individually numbered in the garment to aid in determining the location of the lung and heart sounds. Thus, the acoustic sensors or microphones may be site specific such that each recorded sound may be pinpointed back to a specific microphone along the garment.

The microphones may be positioned anywhere along the garment. The microphones may be located on a front portion of the garment that contacts a chest of the patient. The microphones may also be located on one or more sides of the garment located along a ribcage of the patient. Additionally, the microphones may be positioned along a back side of the garment adjacent to the patient's back. Thus, it is envisioned that the microphones may be highly customizable and tunable based on the desired recordings needed. Additionally, the microphones may be removable for easy replacement if damaged, further modification, or both.

The microphones may include a rubber ear. The rubber ear may encompass all or a portion of the microphones. The rubber ear may function to funnel sound more accurately from a patient into the microphone for accurate recordings. The rubber ears may contact a patient's body and protect the microphone from direct contact with a patient. Thus, the rubber ears may ensure a longer life for each microphone without needing frequent replacement. Additionally, the rubber ears may be flexible or rigid. However, it is envisioned that the rubbers ears may be flexible to at least partially form a patient's body contour, thereby creating a better funnel and seal for directing a sound from the patient's organs into the microphone.

It is contemplated that the garment and microphones may be high portable. As such, the garment may be free of any external wires and may not require and power source to conduct testing on a patient. Therefore, the garment may include one or more power sources, such as a battery or other power source to power the microphones along the garment. The battery may be any battery, such as a lithium ion battery, that may be secured along or within the garment. For example, the battery may be stitched into one or more layers of the garment in a manner that does not obstruct the accurate recordings of the microphones. The battery may be rechargeable, replaceable, or both without damaging the garment. The battery may include a port to connect a cord purely for recharging purposes. Therefore, the garment may advantageously be used a number of times for remote patients regardless of where the patient is located.

By providing a substantially self-sufficient medical testing garment, the garment may record a desired number of data points for further evaluation and analysis. The data points may be collected from the plurality of microphones and then compiled to create a final report. The data compiled may be transmitted (via one or more transmitters of the garment) to a computing device. The computing device may perform one or more processes and/or manipulations on the data received from the garment before outputting a report or final analysis. For example, the data may be initially filtered to remove any unwanted "white noise" present when collecting the data. Additionally, the data may also be amplified to a desired sound level before compiling and interpreting the data.

As one non-limiting example, data from a plurality of microphones may undergo filtering, buffering, and/or amplifying of the soundwaves to produce a signal. The signal may then be converted from analog format to digital format. The signal may then be filtered. The signal may then be normalized. At that point, the normalized signal may be analyzed and transmitted. It should be noted that any one or more of the above processes may be completed in the garment itself, in the external computing device or both. Once the normalized signal is established, the data may be fully analyzed and/or output in a final report, thereby providing a medical professional succinct data to evaluate a patient's current condition.

The garment may be adapted for transmitting data (e.g., through a wired or wireless connection). The data may be collected and may optionally be stored on a hardware device associated with the garment which may be a computing device, or which may transfer data to a computing device. Any of the detection devices described herein (the stethoscope, the microphone, the electrocardiogram leads, the probe, the pulse oximeter, otoscope, oralscope, ophthalmoscope, PanScope, oral temperature device) may facilitate collection of data and may be adapted to transmit the data to a hardware associated with the garment. Alternatively, any of the detection devices described herein may be adapted to transmit data directly to a computing device.

The devices associated with the garment may be embedded in the garment or removably attached to the garment. The devices may be located into pockets formed on the garment. The devices may be fastened to the garment by one or more of a strap, a hook, a snap, a flexible band, or any mechanical fastening device.

The medical device system may also include a glove. The glove may function to provide at least a partial medical evaluation of a patient by recording, tracking, or otherwise collecting key medical data. The glove may then transfer such data offsite from a patient's location (e.g., the patient's home) to an offsite physician or the like. The glove may be utilized by any patient desiring examination and treatment for a number of medical conditions while remaining in their own home. For example, the glove may be used during a pandemic where travelling to a medical facility poses a health threat to the patient. The glove may be delivered to the patient first to conduct an initial examination and gather vitals or other critical data from the patient. Based upon the data collected from the glove, the medical professional may then determine if further evaluation is needed using or if the patient is not at risk and requires no further examination.

The glove may include a plurality of electrocardiogram (EKG) leads. Advantageously, the glove my conduct a 12-lead EKG by positioning the glove directly on the patient in one or more positions to collect enough data from the leads to create a full 12-lead EKG report for a medical professional. It should also be noted that while a 12-lead EKG is discussed herein in further detail, any number of EKG leads may be incorporated. For example, the glove may include more than 12 EKG leads or less than 12 EKG leads. Additionally, each EKG lead may be positioned and recorded a single time during an EKG test, or one or more of the EKG leads may be positioned and recorded multiple times. As a result, the glove may provide significant flexibility in developing a robust and accurate EKG of a patient by recording any number of leads.

The electrocardiogram leads may be integrated into the glove or may be located onto a separate substrate that is secured to the glove when worn by a patient. For most accurate results, the electrocardiogram leads may make direct contact with the patient's skin free of any conventional adhesives, thereby allowing the electrocardiogram leads to be used for numerous tests. The electrocardiogram leads may be positioned anywhere along the glove. For example, the electrocardiogram leads may be positioned in different configurations based on the size, height, weight, etc. of a patient conducting the self-exam. While either a left-handed glove or a right-handed glove may be utilized based on the teachings herein, it is envisioned that a right-handed glove may provide a patient the greatest flexibility to accurately contact their chest and conduct a proper EKG. Specifically, because the heart is located on the left side of the chest cavity, a right-handed glove will allow a patient to conduct a proper EKG more easily with a larger range or motion.

The electrocardiogram leads may be positioned along a peripheral edge of the gloves, one or more fingertips of the glove, a central portion of the glove, or a combination thereof. The electrocardiogram leads may be located on the backside of the glove, the inside palm portion of the glove, or both. The electrocardiogram leads may include precordial electrocardiogram leads, an aVF electrocardiogram lead, one or more aVL and/or aVR electrocardiogram leads, or a combination thereof. Thus, the glove may be positioned along the user's chest, sternum, or both to gather data for each required electrocardiogram lead, thereby allowing a computing device to calculate and compile an overall EKG. It should be noted that the glove may include a battery or power source to facilitate recording and transmitting the data from the electrocardiogram leads or other devices.

Advantageously, unlike a conventional EKG requiring adhesively attached leads secured to a patient's skin, the electrocardiogram leads of the glove may require no adhesive and may be moved along a patient's skin with ease. Furthermore, the electrocardiogram leads may wirelessly transmit data to a computing device, thereby improving the transportability of the glove when compared to a conventional EKG device. As a result of the wireless transmittal, the glove may be positioned anywhere along a patient's body that is reachable by the patient themselves. The glove may be positioned horizontally along the chest and/or sternum of the patient, vertically along the chest and/or sternum of the patient, or anywhere in between. Additionally, spacing may be established by the patient wearing the glove such that the electrocardiogram leads are spaced apart a sufficient distance for accurate data measurements. For example, the electrocardiogram leads may be located on various fingertips so that fingers may be spaced apart and pressed against the patient's skin for measurement. The distance between the electrocardiogram leads may depend on the patient, but the angle formed between the electrocardiogram leads on fingers of the gloves may be about 45 degrees or more, about 90 degrees or more, or about 135 degrees or more. The distance may be about 180 degrees or less, about 160 degrees or less, or about 140 degrees or less. As discussed above, the positioning of the electrocardiogram leads may be adjusted to most accurately record all electrocardiogram leads and accurately record a proper EKG. Thus, the electrocardiogram leads may be positioned and/or repositioned one or more times to accurately record the electrocardiogram lead readings. For example, the aVL and AVR electrocardiogram leads may be recorded substantially simultaneously by positioning both leads on the patient, or alternatively, the aVL and AVR may be recorded separately by positioning each lead individually. As such, it may be gleaned that the glove allows for great customization and flexibility when recording data from electrocardiogram leads.

The glove may also include one or more additional devices. For example, the glove may include a blood pressure cuff to measure blood pressure, a pulse oximeter to measure blood oxygen saturation, a microphone similar to those of the garment, or a combination thereof. The microphone may be positioned along the patient to record sounds from one or more positions, thereby allowing patients to conduct full cardiopulmonary auscultation in the same manner a physician would conduct heart and lung auscultation. For example, the microphone of the glove may be positioned along an upper portion of the chest over the heart, a lower portion of the chest over the heart, along a patient over one or more both lungs, or a combination thereof. Similarly, the microphone (e.g., a digital stethoscope) may be positioned on chest and back concurrently to imitate similar recording provided when a patient were to use a vest as described herein.

The glove may also include one or more position location sensors. The position location sensors may determine a position of the glove along a patient's body. As a result, data can be accurately recorded and correlated to a specific location without manually dictating a proper location. Additionally, it is envisioned that the position location sensors may be used to establish initial testing parameters for the glove. For example, the position location sensors may be moved around a perimeter of a testing area to provide a baseline of where the glove is in relationship to one or more organs of the patient (e.g., the heart, the lungs, etc.). By establishing a baseline, all subsequent testing conducted using the stethoscope, one or more EKG leads, or a combination thereof may be accurately correlated to a specific location within the boundaries of the perimeter initially established. Additionally, it may then be possible to determine any "outliers" during testing for any recorded locations that do not fall within the specific boundaries.

Thus, based on the above, the electrocardiogram leads may collect data in conjunction with the one or more additional devices (e.g., the microphone) to complete a full EKG workup on a patient. It should be noted that the data collected from the glove may be transmitted in a similar manner as the data collected from the garment. For example, the data may be transmitted and thereafter augmented, organized, or manipulated (i.e., filtered, amplified, or both) before outputting an organized data report for a medical professional to evaluate.

The medical device system may include a club designed primarily for abdomen examination. The club may function to provide at least a partial medical evaluation of a patient by recording, tracking, or otherwise collecting key medical data. The club may then transfer such data offsite from a patient's location (e.g., the patient's home) to an offsite physician or the like. The club described herein may be utilized by any patient desiring examination and treatment for most medical conditions while remaining in the comfort of their own home.

The club may be used to provide separate and independent testing of a patient by conducting an abdomen exam on the patient. The club may be used in addition to the garment, the glove, the chair, or a combination thereof to conduct such abdomen exams. For example, the club may include a microphone (e.g., a digital stethoscope) to record sounds within a specific location on the patient's body. Additionally, the club may include a position location sensor to determine a specific location where data is being recorded.

It is envisioned that the club may be used to determine specific locations of pain along a patient's body. To do so, the club may include a mechanism that applies pressure or otherwise contacts the patient. When a patient feels discomfort in a specific location, the club may then record a location for further evaluation by a medical professional. To further determine the severity of any discomfort, the club may also include one or more pressure sensors to more accurately record how much pressure is applied to an area of discomfort, thereby even further allowing accurate analysis of a patient's health concerns.

In addition to locations of pain, the club may also search for tenderness along a patient's body, such as in their head, chest, back, limbs, abdomen, or a combination thereof. To determine such tenderness, the club may include a mechanism that contacts the patient's skin and delivers a percussion into the patient's body. That percussion may then be evaluated and interpreted for tympanicity or dullness. Additionally, the club may check for rebound tenderness by exhibiting a sudden release of a contact point using a quick-release mechanism.

To allow for such percussion, the club may include a structure that "taps" the patient's skin and creates that percussion. The structure may include a rotary mechanism, spring, actuator, motor, gears, or a combination thereof that actuates one or more tapping mechanisms. The structure may be manually or electrically operation. The mechanism may be battery operated. The structure may be any mechanism that allows for a "tapping" motion to be delivered to a patient.

The contact by the structure may be done by one or more small arms that act as a tapping mechanism. The tapping mechanisms may extend from the rotary mechanism, actuator, motor, gears, or the like and may be actuated by the rotary mechanism, actuator, motor, gears, or the like. The tapping mechanisms may extend in any desired direction. In addition to the tapping mechanisms, the club may include one or more devices, such as a microphone, sensor, or both. Thus, it is envisioned that the club may receive the reflected sound waves created by tapping after striking the abdomen internal organs or masses, thus creating an ultrasound-like picture and/or sound that can detect organomegaly, the presence of masses, or both. As a result, the tapping mechanisms may create the percussion and a patient may provide an input on the trigger or other input device to indicate pain in a given position.

The medical device system may also include a chair. The chair may function to provide at least a partial medical evaluation of a patient by recording, tracking, or otherwise collecting key medical data. The chair may then transfer such data offsite from a patient's location (e.g., the patient's home) to an offsite physician or the like. The chair described herein may be utilized by any patient desiring examination and treatment for most medical conditions while remaining in the comfort of their own home.

The chair may be used in conjunction with, or in lieu of, the glove, the garment, or both to perform a self-evaluation on a patient. Thus, the chair may include one or more devices similar to the glove, the garment, or both. For example, the chair may include one or more microphones similar to those of the garment and the glove. However, the chair may also include one or more additional devices different than the glove and the garment. It should be noted that the devices of the chair may be powered by a power source within the chair, such as a battery.

The chair may include one or more straps. The straps may function to at least partially encompass a patient seated in the chair. The straps may be secured around at least a portion of the patient, such as their chest, torso, abdomen, or a combination thereof. The straps may be outfitted with electrocardiogram leads, microphones, other devices, or a combination thereof. Each strap may include a variety of devices or may be designed for one particular type of testing. For example, a first set of straps may include electrocardiogram leads to conduct a proper EKG of a patient while a second set of straps may include one or more microphones to detect and/or record sounds from within the patient. It should be noted that the straps may be used simultaneously or may be used sequentially.

The straps may be any flexible material that may follow a contour or a patient's body. The straps may be a fabric, plastic, or both. The straps may include one or more fasteners, clips, buckles, or a combination thereof to secure the straps to each other, to the chair, or both. The straps may be located anywhere along the chair to properly contact a patient in a desired location. The straps may also include armholes to further facilitate close contact with the body of a patient, thereby allow the patient to at least partially "wear" the straps during testing, as further described herein.

The chair may also include one or more additional devices. The additional devices may include one or more pressure sensors. The pressure sensors may detect the presence of a patient sitting in the chair. The pressure sensors may detect a weight or locally applied force by a patient. The pressure sensors may provide an initial signal to begin testing. For example, the pressure sensors may be located along the chair to ensure a proper posture of the patient prior to conducting a self-examination. Thus, the pressure sensors may be located on a seat of the chair, a back of the chair, or both.

The chair may include one or more microphones embedded directly within a back of the chair, a wearable garment connected to the chair, or both. The microphones may be the same or different to those within the glove, the garment, or both. The microphones may be location specific to determine where specific recording occur. The microphones may be flexible, such as by utilizing a rubber ear, to follow a contour of a patient's body.

The chair may also include one or more air compartments. The air compartments may fill with air to identify locations of pain and/or discomfort of a patient sitting in the chair. The air compartments may be any desired size and/or shape. The air compartments may be positioned anywhere along the chair to strategically contact desired portions of the patient's body. The air compartments may be controlled by the patient in the chair or may be remotely controlled via the computing device or other external remote by a medical professional.

The computing devices and/or the data gathered by the one or more devices with the medical device system may be accessible by one or more of a physician office (e.g., a physician, a physician's assistant, a nurse practitioner, a nurse, a medical resident, a medical assistant, a medical billing associate, or other medical office staff), a pharmacy, a caretaker, a family member, an emergency medical treatment professional, an insurance company, or any individual who may take an action based upon the data. The office and/or individual receiving the data is then able to make medical diagnosis decisions based upon the data. It is possible that the computing device may also replace the human doctor as it may be programmed so that it can establish a diagnosis, recommend testing, and/or prescribe medications.

The computing device may receive data from the medical device system (i.e., the chair, the glove, the garment, or a combination thereof), transmit data to the medical device system, or both. Thus, the computing device may have a receiver, a transmitter, or both in communication with the rest of the medical device system to create two-way communication, three-way communication, or even four-way communication. The computing device may be located anywhere in wireless connection with the medical device system. Thus, the computing device may communicate with the devices of the medical device system via wireless connection such as Bluetooth. However, the computing device may also communicate using the internet (e.g., wi-fi) or a corded connection. It should be noted that the computing device may be any electronic device, such as a table, mobile phone, computer, etc.

Turning now to the figures, FIG. 1 illustrates a perspective view of a medical device system 10. The medical device system 10 includes a garment 12, a glove 14, a chair 40, or a combination thereof in communication with a computing device 50. The garment 12 includes a plurality of microphones 16 that are configured to detect and record sound from a user's heart, lungs, or both. It is envisioned that the user wears the garment similar to a conventional jacket such that the plurality of microphones 16 are located along a user's body adjacent to the user's heart, lungs, or both to record sounds emanating from the heart, lungs, or both. As a result, the plurality of microphones 16 may create a sound pulmogram, a sound cardiogram, or both that is communicated from the garment 12 to the computing device 50.

The medical device system 10 may also include a wearable glove 14 to record one or more vitals of a user. For example, as illustrated in FIG. 1, the glove 14 may include a pulse oximeter 22 that records a user's oxygen saturation. The oxygen saturation levels may then be communicated from the glove 14 to the computing device 50. Additionally, as further described below, the glove 14 may include a microphone 16, such as a digital stethoscope, and one or more electrocardiogram leads 24 to complete a full EKG, complete accurate auscultation of the hearts and/or lungs, or both by moving the glove 14 to one or more desired positions anywhere along the patient. For example, the glove 14 may record heart and lung sounds via the microphone 16 in one or more predetermined locations. The predetermined locations may be determined by an associated medical software system instructing examination using the glove 14. Similarly, the glove 14 may also include a position location sensor (see FIG. 4) that may track a position of the glove 14 while the microphone 16 of the glove 14 creates a comprehensive sound map when the patient moves the glove 14 along their chest to one or more locations.

Furthermore, the vitals data recorded, such as the oxygen saturation level of a user or auscultation results, may then be transmitted directly to the computing device 50 or may pass through one or more manipulation steps to organize or modify the data prior to transmitting the data to the computing device 50. As a result, the data may be interpretated by a medical professional after being received by the computing device 50.

Additionally, the medical device system 10 may include an interactive chair 40. A user may be seated in the chair 40 in an upright position so that the chair 40 may collect a variety of vitals or other data from a user and transmit such data to the computing device 50 via a transmitter 30 located along the chair 40 to help diagnose potential health conditions. To collect the user data and help diagnose health conditions, the chair 40 may include one or more microphones to record sound from the user's body, one or more air compartments 36 to determine potential pain locations along a user's body, or both. Additionally, the chair 40 may include one or more pressure sensors to determine a user's weight, to determine when a user is present in the chair 40, or both.

For example, a user may sit in the chair 40 so that the pressure sensors sense a presence of the user. The pressure sensors may be in different locations along the chair 40 to ensure a desired posture of the user. One configuration may include a first pressure sensor located on a seat of the chair 40 and a second pressure sensor located on a back of the chair 40. Accordingly, the chair 40 may detect that a user is properly seated in the chair 40 with their back against the back of the chair 40. However, it should be noted that the pressure sensors located along the chair 40 may be positioned in any desired location to sense a positioning and/or posture of a user. Additionally, the chair 40 may be configured remotely from the computing device 50 (or any other external device) by receiving a command and/or signal via a receiver 28 of the chair 40. Further details and configurations of the chair 40 are discussed below to describe the chair 40 shown in FIG. 7.

It is envisioned that that garment 12, the glove 14, and the chair 40 may each be utilized individually as a sole device for a patient to measure and record vitals or other data based upon the patient's body. The recorded data may then be processed or otherwise manipulated to evaluate the health of the patient. As such, it should be noted that the garment 12, the glove 14, or both may also include one or more transmitters 30, one or more receivers 28, or both to communicate with the computing device 50 so that the recorded data from the garment 12, the glove 14, or both is transmitted to the computing device 50 for further analysis. Beneficially, the computing device 50 may be located near the devices 12, 14, and 40, or may be located at an offsite location such that a patient may conduct their testing using the medical device system 10 free of physical interaction with a medical professional. Additionally, the medical device system 10 may allow for a patient who may otherwise be unable to easily reach a medical facility gain proper medical care. For example, during a pandemic, a patient may easily gain medical care via the medical device system 10 without a need to enter a medical facility and risk exposure to a health threat.

The computing device 50 may also include a transmitter, a receiver, or both that communicate with the garment 12, the glove 14, the chair 40, or a combination thereof. Thus, the computing device 50 may wirelessly, or via one or more cables, transmit data to and from the garment 12, the glove 14, the chair 40, or a combination thereof. As a result, a medical professional may receive the data from the devices 12, 14, and 40 on the computing device 50 to help diagnose a potential medical condition of the patient. Additionally, due to two-way communication between the computing device 50 and the other devices 12, 14, and 40, the computing device 50 may also send various data and/or commands to the devices 12, 14, and 40. For example, the computing device 50 may send a signal to initiate operation of the devices 12, 14, and 40, change settings or configurations of the devices 12, 14, and 40, or both.

FIG. 2 illustrates a perspective view of a garment 12 in accordance with the present teachings. The garment 12 may include a plurality of microphones 16 distributed along one or more sides of the garment 12. For example, as illustrated, the microphones 16 may be located on a front of the garment 12A, one or more sides of the garment 12C, a back of the garment 12B, or a combination thereof. It is envisioned that the microphones 16 may be site specific such that, when the garment 12 is worn by a patient, the microphones 16 align with one or more organs of the patient. For example, at least a portion of the microphones 16 may align with the lungs of the patient, the heart of the patient, or both to detect and/or record a sound emitted from the lungs, the heart, or both to analyze the auscultation thereof. Due to a plurality of microphones 16 being utilized to track the sound of the organs, the garment 12 may advantageously compile a plurality of sounds from various positions to create a sound pulmogram, a sound cardiogram, or both. The microphones 16 may be positioned to at least partially surround the one or more of the organs (such as the lungs and/or heart) such that converging data taken from the microphones 16 creates an accurate sound pulmogram, a sound cardiogram, or both.

Furthermore, the garment 12 may include one or more electrocardiogram leads 24 to complete a full EKG of a patient. It is envisioned that the electrocardiogram leads 24 may complete a full 12-lead EKG. However, the garment 12 may beneficially allow for additional electrocardiogram leads 24 to receive further data points. For example, the electrocardiogram leads 24 may be located on both a front side of the garment 12 aligned with the chest of a patient and the back side of the garment 12 aligned with the back of a patient. Thus, the electrocardiogram leads 24 may receive surface electrical signals from both sides of the heart. It should also be noted that one or more microphones 16 may be located on the back side of the garment 12 as well as the front side.

Each microphone 16 may be surrounded by a rubber ear 34 to more accurate funnel sound from the patient into the microphone 16. Additionally, the garment 12 may beneficially include a battery 32 or other power source located within the garment 12 to power the microphones 16 or one or more additional items, such as a pulse oximeter 22 connected to a sleeve of the garment 12, a blood pressure cuff 26 integrated into a sleeve of the garment 12, or both. Thus, the garment 12 may be used by a patient without being constrained by one or more power cords or other tethers, thereby making the garment 12 significantly transportable. Furthermore, the garment 12 may beneficially communicate with a computing device 50 via a transmitter 30, a receiver 28, or both to send and/or receive data from the computing device 50, thereby further optimizing remote operation of the garment 12.

As shown in FIG. 3, the microphones 16 may record sounds from the patient's body and communicate those sounds to a computing device 50. While the sounds may be recorded and transmitted directly to the computing device 50 free of manipulation, one or more processes may take place to adjust the sounds recorded prior to a final output of data on the computing device 50 for a medical professional to evaluate. One such process is shown in FIG. 3.

As illustrated, the microphones 16 along the garment 12 may first collect data (e.g., sound) from a patient. The microphones 16 may be site specific such that each data point collected is associated with a specific microphone location, thereby allowing a medical professional to even further pinpoint a targeted medical condition. For example, each microphone 16 may record a site-specific signal so that the plurality of signals recorded by the microphones 16 may be combined to create a sound pulmogram, a sound cardiogram, or both. Once the data is recorded from the microphones 16, the data may then pass through a filtration process. The filtration process may filter out any "white noise" or other extraneous portions of the data recorded by the microphones 16. The filtered data may then pass through an amplification process (if needed) to amplify the sounds recorded by the microphones 16 and place the data in a condition for evaluation. It should be noted that the filtration and amplification of recorded data from the microphones 16 may be completed on each data point from each target specific microphone 16, or may only be completed on a portion of the data points from the microphones 16. After amplification, the data from all of the microphones 16 may be compiled (i.e., summed) in preparation of interpretation. Some or all of the interpretation may be completed by programming on the computing device 50. However, a final output of data on the computing device 50 may still require interpretation or further evaluation from one or more medical professionals.

As may be gleaned from the process above, the garment 12 may compile the data in a beneficial manner such that a medical professional receives a final test result or report for evaluation. For example, the microphones 16 may be provide sufficient data to create a full sound pulmogram, a sound cardiogram, or both. In doing so, the medical professional may also be able to remotely obtain certain patient vitals and create a complete cardiogram of the patient using the medical device system 10. Thus, the medical device system 10 may provide test results sufficient for a medical professional to: evaluate heart sounds of the patient; detect the presence of an issue, including location, strength, type, quality, or a combination thereof of the murmur; a rhythm or the patient's heart; the patient's heart muscle function; or a combination thereof.

Figure 4:
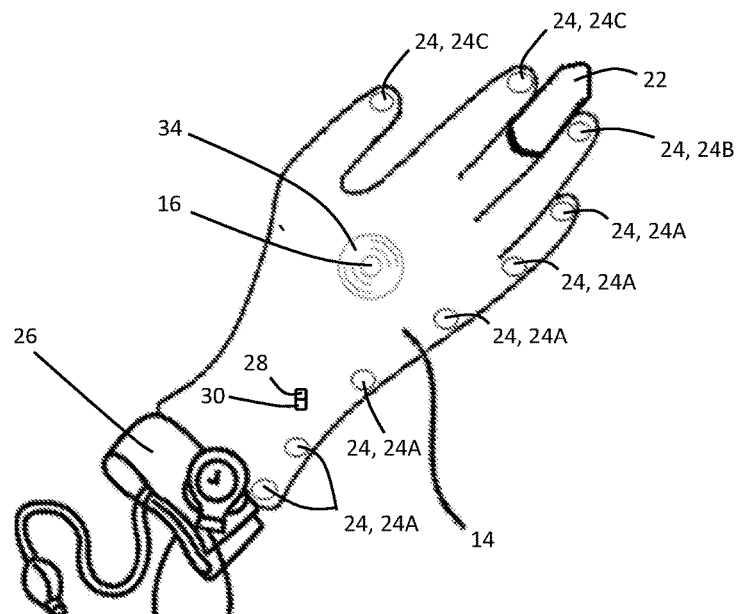
FIG. 4 is a perspective view of a glove of a medical device system.

As shown in FIG. 4, the glove 14 of the medical device system 10 may be used in lieu of the garment 12 described in FIGS. 2 and 3. The glove 14 may also include one or more microphones 16 surrounded by a rubber ear 34 to detect sounds from a patient's body. Additionally, the glove 14 may include a pulse oximeter 22 to determine the patient's oxygen saturation levels. The pulse oximeter 22 may be integrally formed, or connected to, one or more finger holes of the glove 14. To even further check vitals of the patient, the glove 14 may include an integrated blood pressure cuff 26 to check a blood pressure of the patient at a wrist and/or an elbow of the patient. It is envisioned that the glove 14 may include a sleeve such that the blood pressure cuff 26 may be located along the sleeve to more accurately measure blood pressure of a patient near their elbow.

Furthermore, the glove 14 may include a plurality of electrocardiogram leads 24. It is envisioned that the electrocardiogram leads 24 may be positioned along a patient's body in one or more desired positions to records data and create a 12-lead electrocardiogram (EKG). However, it should be noted that the glove 14 may utilized to record a plurality of data points and create an EKG having greater than 12 leads. For example, a 24-lead EKG recording may be possible by utilizing electrocardiogram leads 24 of the glove 14 for multiple recordings in different locations.

The glove 14 may include, for example, six precordial EKG leads 24A, an aVF EKG lead 24B, and a pair of aVL/aVR EKG leads 24C, that are positioned along the patient in various locations to complete the full 12-lead EKG. These positions are further illustrated in FIGS. 5A-5D below. The data recorded by the glove 14 may then be transmitted by a transmitter 30 of the glove 14 to an external computing device (see FIG. 1). Similarly, the glove 14 may also include a receiver 28 to receive any commands and/or data from an external computing device to configure the glove 14, being testing utilizing the glove 14, or both.

Figure 5A:
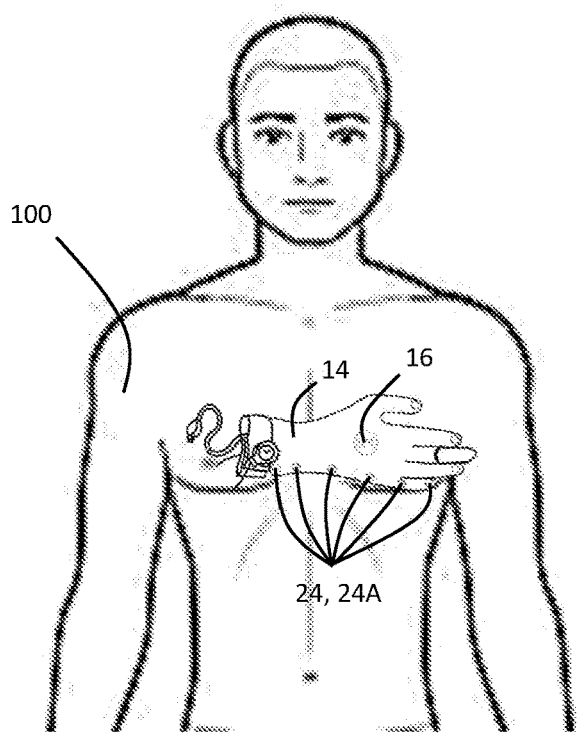
FIG. 5A is a first position of a glove on a user to record precordial electrocardiogram leads of a 12-lead electrocardiogram recording.

A first position of the glove 14 along a patient 100 is shown in FIG. 5A. As shown, the glove 14 is held in a substantially horizontal position and pressed against the chest of the patient 100. In this position the precordial electrocardiogram leads 24, 24A are recorded. It should be noted that while the precordial EKG leads 24A are recorded in Position A, any of the EKG leads 24 may be recorded in any desired location. Additionally, the microphone 16 may also be utilized in any of the positions described herein to record data within the patient's 100 hand, the patient's 100 chest, or both. Thus, it may be gleaned from the present teachings that in addition to the glove recording data via the electrocardiogram leads 24, the microphone 16 of the glove 14 may beneficially allow a patient to conduct proper auscultation of the heart and/or lungs by positioning the microphone 16 along the chest and/or back over the heart, the lungs, or both.

Figure 5B:
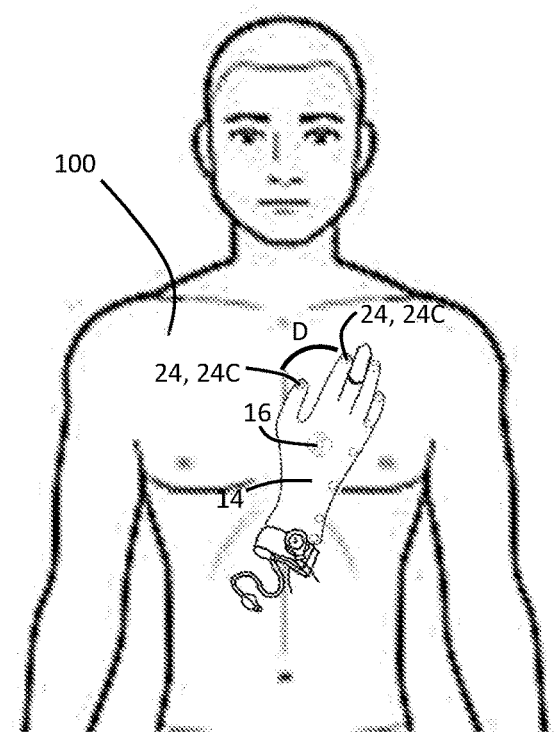
FIG. 5B is a second position of a glove on a user to record aVL and AVR electrocardiogram leads of the 12-lead electrocardiogram recording of FIG. 5A.

As shown in FIG. 5B, after recording the precordial EKG leads 24A, the glove 14 is once again positioned on the patient's 100 chest, but now in a substantially vertical position with the thumb and index finger pointing toward the patient's 100 head. It is envisioned that the thumb and index finger are opened as widely as possible to create a significant distance (D) (e.g., greater than 100 degrees) between the thumb and index finger. As a result, the aVL and aVR EKG leads 24, 24C located on the thumb and index finger may be spaced apart and pressed against the skin of the patient 100 on their chest. Thus, the aVR and aVL EKG leads 24, 24C may be recorded.

Figure 5C:
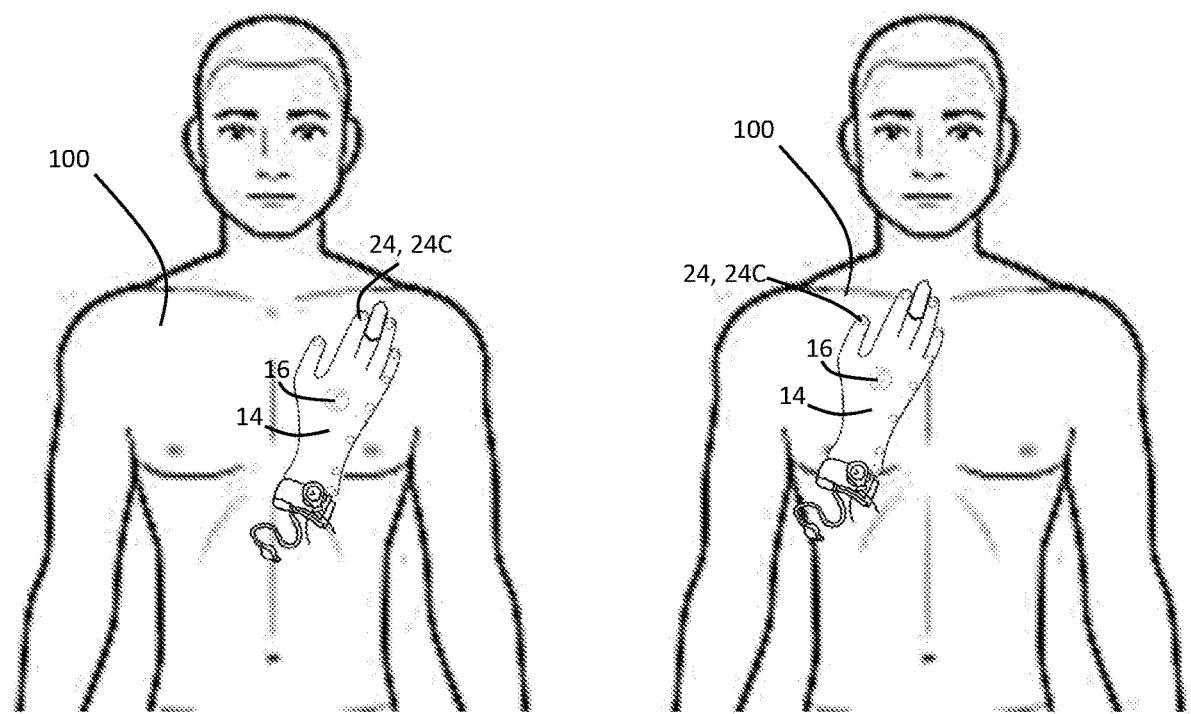
FIG. 5C is a third position of a glove on a user to record aVL and AVR electrocardiogram leads of the 12-lead electrocardiogram recording of FIG. 5A.

However, as shown in FIG. 5C, a second position may be necessary for properly recording the aVR and aVL EKG leads 24, 24C. For example, it is envisioned that some patients may not have adequate spacing between their thumb and index finger to provide a large enough distance (D) between their thumb and index finger. As a result, the recording of the aVR and aVL leads 24, 24C may not be accurate. To combat such an inaccuracy, a patient 100 may first record the aVL lead 24, 24C using their index finger. Afterwards, the patient 100 may then move the glove 14 and record a proper aVR lead 24, 24C using their thumb. As such, the glove 14 may separately record the aVL and aVR leads 24, 24C in any order and not require simultaneous recordings.

Figure 5D:
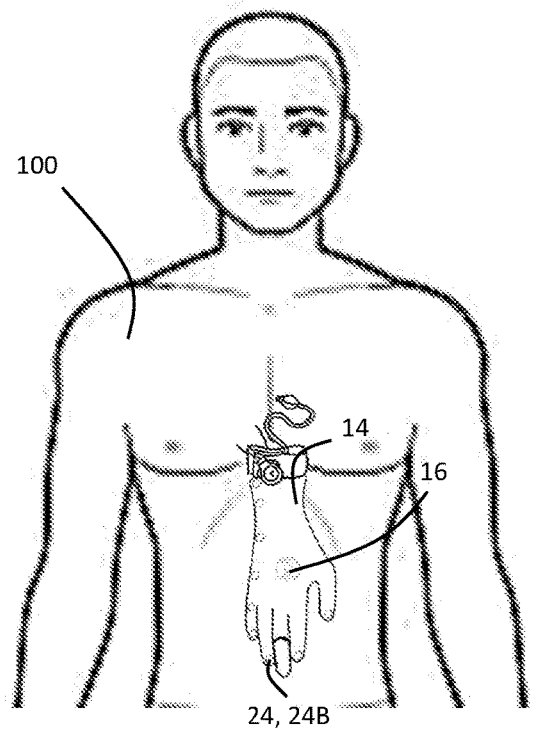
FIG. 5D is a fourth position of a glove on a user to record an aVF electrocardiogram lead of the 12-lead electrocardiogram recording of FIGS. 5A and 5B.

Lastly, as shown in FIG. 5D, after recording of the aVR and aVL EKG leads 24, 24C, the glove 14 may be positioned in a substantially vertical position with the middle finger of the glove 14 positioned downward and pressed against the mid or lower abdomen of the patient 100. As a result, the aVF EKG lead 24, 24B located on the middle finger of the glove 14 may be pressed again the mid or lower abdomen of the patient 100 to record the aVF EKG lead 24, 24B.

Thus, after completion of the recordings taken in FIGS. 5A-5C, a 12-lead EKG may be compiled. The recordings of the electrocardiogram leads 24 may then be combined with the data recorded by the microphone 16, the pulse oximeter 22, and the blood pressure cuff 26 of the glove 14. This data may then be transmitted from the glove 14 to a computing device for a medical professional to evaluate (see FIG. 1). It should be noted that, like the data recorded using the garment 12 shown in FIG. 3, the data recorded by the glove 14 may be augmented or otherwise manipulated to adjust and/or organize the data recorded. This may include one or more steps or filtration, amplification, or both. Once the data is organized, the external computing device may then generate and display a report for a medical professional to evaluate.

Figure 6:
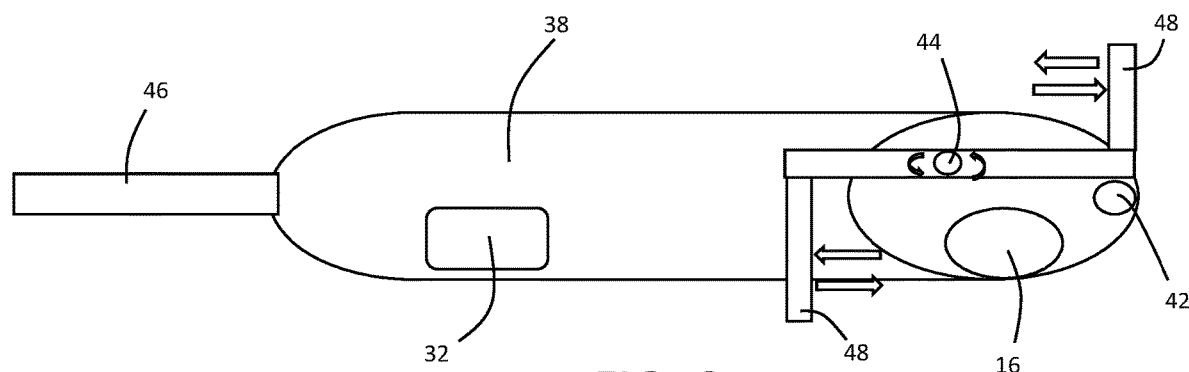
FIG. 6 is a perspective view of a club in accordance with the present teachings.

FIG. 6 illustrates a perspective of a club 38 in accordance with the present teachings. It is envisioned that the medical device system described herein may also include the club 38 in addition to the garment, the glove, and/or the chair (see FIG. 1). The club 38 may be used in addition to the garment, the glove, the chair, or a combination thereof within the medical device system to conduct an abdomen examination. However, it should be noted that the club 38 may also be used for further examination of a patient other than an abdomen, such as the heart, lungs, eyes, ears, throat, or a combination thereof. Thus, beneficially, the medical device system may be tailored to a specific patient and may include any number of the devices described herein to evaluate a patient most effectively by providing a plurality of devices to conduct a comprehensive physical examination of the patient.

The club 38 may include a handle 46 to allow for a patient to grasp the club 38 during operation. The handle 46 may extend from a proximal end of the club 38 such that one or more accessories along the club 38 are positioned near an opposing distal end. The club 38 may include a microphone 16 (e.g., a digital stethoscope) to allow a patient to detect and/or record internal sounds from within their own body by positioning the microphone 16 in a desired location. The club 38 may further include a position location sensor 42 disposed along an outer surface of the club 38. The position location sensor 42 may pinpoint a location of potential discomfort for a patient. For example, the club 38 may include a rotary member 44 connected to one or more tapping mechanisms 48, shown as projecting arms. The rotary member 44, whether manually or electronically, may drive a movement of the tapping mechanisms 48 such that the tapping mechanisms 48 tap or otherwise engage a patient's body. As shown, if electronically actuated, the rotary member 44 may be driven by an integrated battery 32 of the club 38. The movement of the tapping mechanisms 48 may be utilized to safely apply pressure to a patient to determine any localized pain along the patient's body. When a location is "tapped" and the patient feels discomfort, the position location sensor 42 may determine a location along the patient's body, thereby more accurately evaluating potential causes of the discomfort. The position location sensor 42 may also be used to establish initial parameters of testing by creating a baseline perimeter along the patient prior to conducting testing. It is envisioned that the 38 may be moved along a patient's body, either by themselves or a third party, to evaluate any and all locations of discomfort in an effective manner.

It should be noted that the club 38 may include any number of tapping mechanisms 48, position location sensors 42, or microphones 16. Additionally, the rotary member 44 may be any actuating member that drives a motion of the arms 48 to "tap" the patient's body. The actuating member may be an electronic actuator or an actuating mechanism that requires manual operation.

While the club 38 may target areas of pain or discomfort of a patient, the club 38 may also be utilized to determine dullness (e.g., the sound resulting from a tapping on a solid organ or mass), rebound tenderness, tympanicity, organomegaly, other potential health concerns, or a combination thereof. For example, the tapping mechanisms 48 may deliver percussion during the "tapping" operation, thereby sending a wave through a location on the patient's body (e.g., the abdomen). That percussion may then be analyzed to interpret tympanicity, dullness, or both. In other words, the club 38 may help a medical professional determine if a part of the patient's body, such as their abdomen, head, chest, back, limbs, or a combination thereof, is soft or hard.

Figure 7:
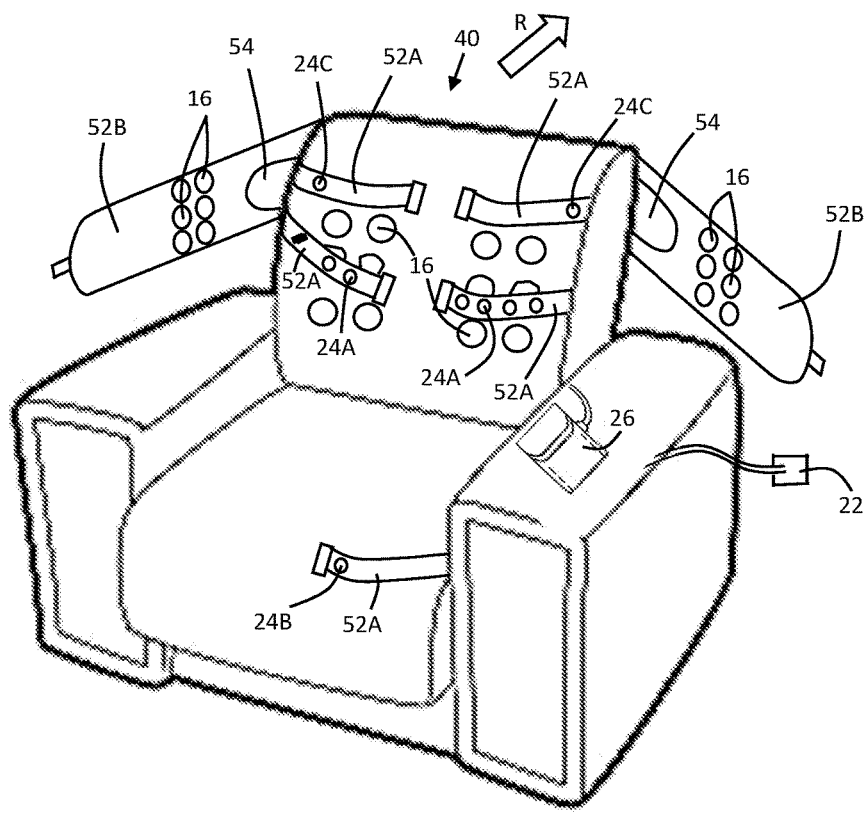
FIG. 7 is a perspective view of a chair of the medical device system.

FIG. 7 is a perspective view of a chair 40 of the medical device system. The chair 40 may be a standard design, size, shape, or a combination thereof. Illustrated in FIG. 7, the chair 40 may be based upon a conventional armchair. The chair 40 may include a plurality of straps 52 that contact a patient's body for collecting data. The straps 52 may include electrocardiogram straps 52A that have a plurality of electrocardiogram leads 24. The electrocardiogram leads 24 may be configured to make direct contact with a patient's skin to conduct an accurate EKG. The electrocardiogram leads 24 may be dispersed along a single strap 52 or may be disposed on a plurality of straps 52. For example, as shown, upper straps 52A may include the aVL and aVR electrocardiogram leads 24C to contact a patient's upper chest while the additional electrocardiogram straps 52A may include the precordial 24A and aVF 24B electrocardiogram leads. It is envisioned that the electrocardiogram straps 52A may be secured across a patient's torso to directly contact their skin. The electrocardiogram straps 52A may include one or more buckles, clips, fasteners, or a combination thereof to tightly secure the electrocardiogram leads 52A around the patient.

Additionally, the chair 40 may also include microphone straps 52B the tightly secure around the patient by allowing the patient to extend their arms through armholes 54 within the microphone straps 52B. Once the microphone straps 52B are secured using a buckle, clip, fastener, or a combination thereof, a plurality of microphones 16 may be disposed along the patient's chest to detect and/or record internal sounds.

The microphone straps 52B may be secured to the patient while the electrocardiogram straps 52A are free of contact with the patient, or vice versa. However, beneficially, the microphone straps 52B and the electrocardiogram straps 52A may both be secured to the patient to form a multi-layer detection system along the patient. Thus, the chair 40 beneficially records and detects a gamut of data simultaneously while a patient remains seated in a single position 40.

To further facilitate diagnosis of a patient's potential medical condition, the chair 40 may also include a blood pressure cuff 26, a pulse oximeter 22, or both. These devices 26, 22 may be positioned anywhere along the chair to allow for proper testing. For example, as shown, the blood pressure cuff 26 and the pulse oximeter 22 may both be connected and/or integrated into an arm of the chair 40. Furthermore, the chair may also include one or more integrated microphones 16 (e.g., digital stethoscopes) that detect and/or record sound from a patient's back, thereby even further establishing a robust data recording system within the chair 40. Additionally, as shown, the chair 40 may also help facilitate comfort for the patient and accurate testing data by including a reclining feature that allows the chair 40 to recline in a desired direction (R).

ELEMENT LIST

10 Medical Device System
12 Garment
12A Front of the Garment
12B Back of the Garment
12C Side of the Garment
14 Glove
16 Microphone
22 Pulse Oximeter
24 Electrocardiogram Lead
24A Precordial Electrocardiogram Lead
24B aVF Electrocardiogram Lead
24C aVL and aVR Electrocardiogram Lead
26 Blood Pressure Cuff
28 Receiver
30 Transmitter
32 Battery
34 Rubber Ear
36 Air Compartment
38 Club
40 Chair
42 Location Position Sensor
44 Rotary Member
46 Handle
48 Tapping Mechanism
50 Computing Device
52 Strap
52A Electrocardiogram Strap
52B Microphone Strap
54 Armhole
100 Patient
R Recline Direction of the Chair The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Unless otherwise stated, a teaching with the term "about" or "approximately" in combination with a numerical amount encompasses a teaching of the recited amount, as well as approximations of that recited amount. By way of example, a teaching of "about 100" encompasses a teaching of 100+/− 15.

The disclosures of all articles and references, including patent applications and publications, are incorporated by reference for all purposes. Other combinations are also possible as will be gleaned from the following claims, which are also hereby incorporated by reference into this written description.

What is claimed is:

1. A glove comprising:
a set of electrocardiogram leads configured to record a 12-lead electrocardiogram by pressing the glove against skin of a user, the set of electrocardiogram leads including:
(a) a plurality of precordial electrocardiogram leads positioned along a peripheral edge of the glove and extending continuously with substantially equal spacing between a wrist portion of the glove and a pinkie of the glove, wherein two of the precordial electrocardiogram leads are positioned on the pinkie of the glove, and an additional two or more of the precordial electrocardiogram leads are positioned on the peripheral edge of the glove and spaced apart from the pinkie;
(b) a pair of aVL and aVR electrocardiogram leads; and
(c) an aVF electrocardiogram lead; and
a digital microphone surrounded by a rubber ear and spaced apart from the set of electrocardiogram leads;
wherein the glove is configured to wirelessly transmit, via a transmitter of the glove, recording data from the set of electrocardiogram leads and the digital microphone to an external computing device.

2. The glove of claim 1, wherein the plurality of precordial electrocardiogram leads are disposed on a palm side of the glove along the peripheral edge of the glove,
wherein the peripheral edge of the glove extends along an outermost edge of the pinkie of the glove, and
wherein the plurality of precordial electrocardiogram leads extend continuously with substantially equal spacing along the outermost edge between the pinkie and an opening of the glove located at the wrist portion of the glove.

3. The glove of claim 1, wherein one of the pair of aVL and aVR electrocardiogram leads is positioned on a fingertips of a thumb of the glove and an another of the pair of aVL and aVR electrocardiogram leads is positioned on an index finger of the glove, and wherein the thumb and the index finger of the glove are free of any other electrocardiogram leads of the set of electrocardiogram leads.

4. The glove of claim 3, wherein the aVF electrocardiogram lead is positioned on a fingertip of a ring finger of the glove.

5. The glove of claim 1, wherein the glove records the 12-lead electrocardiogram by recording data from the set of electrocardiogram leads in 3 distinct positions of the glove configured to be in contact with the skin of the user.

6. The glove of claim 5, wherein the plurality of precordial electrocardiogram leads record data in a first position of the glove, whereby the glove is configured to be disposed horizontally along a chest of the user and orthogonal to a height of the user with the plurality of precordial electrocardiogram leads configured to be in contact with the chest of the user.

7. The glove of claim 6, wherein the pair of aVL and aVR electrocardiogram leads are positioned on fingertips of a thumb and an index finger of the glove; and
wherein the pair of aVL and aVR electrocardiogram leads record data in a second position of the glove, whereby the glove is configured to be disposed vertically along the chest of the user and parallel to the height of the user with the fingertips of the thumb and the index finger spaced apart and configured to be in contact with the chest of the user.

8. The glove of claim 7, wherein the thumb and the index finger of the glove form an angle of at least 100 degrees when in the second position.

9. The glove of claim 7, wherein the aVF electrocardiogram lead is positioned on a fingertip of a ring finger of the glove; and
wherein the aVF electrocardiogram lead records data in a third position of the glove, whereby the glove is configured to be disposed vertically along an abdomen of the user and parallel to the height of the user with the fingertip of the ring finger configured to be in contact with the abdomen of the user.

10. The glove of claim 1, further comprising a sleeve, wherein a blood pressure cuff is located along the sleeve and is configured to measure a blood pressure of the user near an elbow of the user.

11. The glove of claim 10, further comprising a pulse oximeter integrally formed, or connected to, a middle finger of the glove, wherein the middle finger of the glove is free of any electrocardiogram leads of the set of electrocardiogram leads.

12. The glove of claim 1, wherein the digital microphone is positioned centrally along the glove.

13. The glove of claim 1, wherein the glove includes a wireless receive data or commands from the external computing device.

14. The glove of claim 13, wherein data recorded by the glove is processed through a filtration step, an amplification step, or both before being displayed on the external computing device for evaluation.

15. The glove of claim 13, where the data recorded by the glove and transmitted to the external computing device is displayed in a report.

16. The glove of claim 1, wherein the glove is configured to be worn by the user to record their own 12-lead electrocardiogram.

17. A medical device system, including:
(a) the glove of claim 1;
(b) a wearable garment having a plurality of microphones;
(c) a club having one or more tapping mechanisms that create a percussion through a patient; and (d) a chair having one or more sensors;

wherein data is recorded by the glove, the garment, the chair, or a combination thereof and wirelessly transmitted to a computing device for offsite evaluation.

18. The medical device system of claim 17, wherein the plurality of microphones of the garment record sounds to compile a sound pulmogram, a sound cardiogram, or both.

19. The medical device system of claim 18, wherein the plurality of microphones are site specific such that each sound record is associated with a specific microphone location.

20. The medical device system of any of claim 19, wherein the chair includes one or more pressure sensors, one or more air compartments, one or more microphones, or a combination thereof.

* * * * *